United States Patent
Karavas et al.

(10) Patent No.: US 9,561,186 B2
(45) Date of Patent: Feb. 7, 2017

(54) METHOD FOR IMPROVING THE BIOAVAILABILITY OF LOW AQUEOUS SOLUBILITY DRUGS

(71) Applicants: Evangelos Karavas, Pallini Attikis (GR); Efthimios Koutris, Pallini Attikis (GR); Vasiliki Samara, Pallini Attikis (GR); Amalia Diakidou, Pallini Attikis (GR); Georgia Papanikolaou, Pallini Attikis (GR)

(72) Inventors: Evangelos Karavas, Pallini Attikis (GR); Efthimios Koutris, Pallini Attikis (GR); Vasiliki Samara, Pallini Attikis (GR); Amalia Diakidou, Pallini Attikis (GR); Georgia Papanikolaou, Pallini Attikis (GR)

(73) Assignee: PHARMATHEN S.A., Pallini, Attikis (GR)

( * ) Notice: Subject to any disclaimer, the term of this patent is extended or adjusted under 35 U.S.C. 154(b) by 0 days.

(21) Appl. No.: 14/443,094

(22) PCT Filed: Nov. 30, 2012

(86) PCT No.: PCT/EP2012/004958
§ 371 (c)(1),
(2) Date: May 15, 2015

(87) PCT Pub. No.: WO2014/082651
PCT Pub. Date: Jun. 5, 2014

(65) Prior Publication Data
US 2015/0290137 A1    Oct. 15, 2015

(51) Int. Cl.
*A61K 9/20* (2006.01)
*A61K 31/40* (2006.01)
*A61K 31/4535* (2006.01)
*A61K 31/4985* (2006.01)
*A61K 31/42* (2006.01)
*A61K 47/22* (2006.01)

(52) U.S. Cl.
CPC ........... *A61K 9/2013* (2013.01); *A61K 9/2009* (2013.01); *A61K 9/2027* (2013.01); *A61K 9/2095* (2013.01); *A61K 31/40* (2013.01); *A61K 31/42* (2013.01); *A61K 31/4535* (2013.01); *A61K 31/4985* (2013.01); *A61K 47/22* (2013.01)

(58) Field of Classification Search
CPC ... A61K 9/2013; A61K 9/2009; A61K 9/2095
See application file for complete search history.

(56) References Cited

U.S. PATENT DOCUMENTS

2003/0104048 A1* 6/2003 Patel .................... A61K 9/4808
424/451

FOREIGN PATENT DOCUMENTS

| EP | 0670162 A1 | 9/1995 | |
|---|---|---|---|
| NL | WO 2011000581 A2 * | 1/2011 | ........... A61K 9/2018 |
| WO | 2006119498 A2 | 11/2006 | |
| WO | 2011000581 A2 | 1/2011 | |

* cited by examiner

*Primary Examiner* — Yong Chu
(74) *Attorney, Agent, or Firm* — AKC Patents LLC; Aliki K. Collins

(57) ABSTRACT

The present invention relates to the implementation of a new method for manufacturing solid dosage forms for oral administration comprising poorly water soluble active ingredients which overcomes the associated solubility problems and affords improved dissolution profile.

7 Claims, 3 Drawing Sheets

METHOD FOR IMPROVING THE BIOAVAILABILITY OF LOW AQUEOUS SOLUBILITY DRUGS

TECHNICAL FIELD OF THE INVENTION

The present invention relates to a new method for enhancing the solubility and bioavailability characteristics of a poorly water soluble active ingredient and producing an improved oral solid dosage form.

BACKGROUND OF THE INVENTION

The oral route is the most preferable route of active ingredient administration because of several benefits, such as better patient compliance, safety and versatility. Therefore, a vast number of active ingredients is formulated in oral pharmaceutical dosage forms and mostly as solid pharmaceutical preparations, e.g. tablets, chewable tablets, capsules.

Nevertheless, there are some obstacles and difficulties when developing solid forms for oral administration, as many active pharmaceutical ingredients exhibit a low solubility in aqueous fluids which leads to decreased dissolution rate and limited therapeutic effect.

The aqueous solubility of an active ingredient is one of the most important physicochemical properties as low aqueous solubility and low dissolution rate can reduce the active ingredient absorption in the gastro-intestinal tract. Low active ingredient solubility also directs to decreased bioavailability, increased chance of food effect, more frequent incomplete release from the dosage form and higher inter-patient variability.

Poorly water soluble active ingredients, namely compounds having solubility in water below 0.1 mg/ml, consist a large majority of the pharmaceutical active ingredients, thereby limiting their potential uses and increasing the difficulty of formulating bioavailable pharmaceutical products. In this category, disclosed are active ingredients such as Atorvastatin, Leflunomide, Raloxifene and Tadalafil.

Poorly soluble active ingredients have stimulated the development of active ingredient delivery technologies to overcome the obstacles to their solubilization through either chemical or mechanical modification of the environment surrounding the active ingredient molecule, or physically altering the macromolecular characteristics of aggregated active ingredient particles. These technologies include both traditional methods of solubility enhancement, such as particle size reduction, addition of surfactants and inclusion in cyclodextrin-active ingredient complexes, and the use of more novel mechanisms such as self-emulsifying systems, micronisation via nanoparticles, pH adjustment and salting-in processes.

Various methods are already known for the industrial preparation of dosage forms for oral administration comprising active pharmaceutical ingredients having low solubility. However, the prior art has encountered substantial difficulties in the production of oral solid formulations of a desirable bioavailability because of the very poor solubility of said active ingredient.

US-A-2006/068010 relates to a method for improving bioavailability of a low solubility active ingredient comprising orally administering a tablet or capsule comprising granules of said active ingredient with at least one amino acid and at least one intra-granular hydrophilic polymer, an immediate release excipient or a sustained release excipient.

WO-A-2005/041929 claims a solid oral dosage form comprising an active ingredient, a solubilizer and a release modulator, wherein the release of the active ingredient and solubilizer are synchronized.

Although each of the patents above represents an attempt to provide solid dosage forms for oral administration comprising poorly water soluble active ingredients, which overcome the related problems of low aqueous solubility and bioavailability of said active ingredient, there still exists the need for a simple, easy to operate and low-cost innovative process for formulating such active ingredients.

SUMMARY OF THE INVENTION

It is therefore, an object of the present invention to improve the solubility and bioavailability characteristics of poorly water soluble active ingredients.

A further aspect of the present invention is to afford a method for the preparation of a solid pharmaceutical composition for oral administration which overcomes the difficulties encountered in pharmaceutical production because of the low solubility of several active ingredients.

According to another embodiment of the present invention, a cost effective and simple process for manufacturing a solid pharmaceutical composition for oral administration is provided. Dosage forms of different strengths are formulated by proportionally adjusting the amounts of the pharmaceutically acceptable excipients and the active ingredient; thereby providing a pharmacotechnical linearity, without affecting the dissolution profile and bioavailability of the active ingredient.

Another aspect of the present invention is the use of a functional excipient as a dissolution enhancing agent that contains a cyclic amide moiety, preferably a 2-pyrrolidone moiety, preferred excipients are 2-pyrrolidone, N-methyl-2-pyrrolidone and povidone (1-vinyl-2-pyrrolidone homopolymer) for poorly water soluble active ingredients.

In particular, a dissolution enhancing agent for poorly water soluble pharmaceutical active ingredients, as described above, facilitates the release and increases of the bioavailability of the active ingredient, especially in combination with silicon dioxide, especially colloidal silicon dioxide, which displays a synergistic effect.

A feature of the invention is a manufacturing process for a pharmaceutical formulation, or an intermediate granule ready for formulation, is provided. Said method (hereafter referred to as "Pyrroplus Manufacturing Process" or "Pyrroplus") comprises the following stages: dissolving and/or mixing the active ingredient with at least one cyclic amide moiety containing excipient excipient, optionally by stirring;
  mixing the obtained solution/mixture with silicon dioxide, and optionally adding other internal phase excipients;
  wet or dry granulation of the obtained mixture, optionally with ethanol; and, optionally,
  drying the wetted mass, if required, preferably at temperature of around 40° C.

Additional steps used in the manufacture of a solid pharmaceutical dosage form include one of more of the following additional steps:
  passing the dry granule through a sieve to achieve the desired granule size;
  mixing the dry granule with the constituents of the external phase excipients until a uniform mixture is produced;
  compressing the mixture or granules into tablets, optionally with further excipients, in a tableting machine; and/or coating the obtained tablets.

Additionally provided is an amorphous active ingredient adducted to a cyclic amide moiety containing excipient product obtainable by a process comprising; dissolving and/or mixing the active ingredient with at least one cyclic amide moiety containing excipient excipient mixing the obtained solution/mixture with silicon dioxide and drying the mixture.

Other objects and advantages of the present invention will become apparent to those skilled in the art in view of the following detailed description.

DETAILED DESCRIPTION OF THE INVENTION

Figure 1:
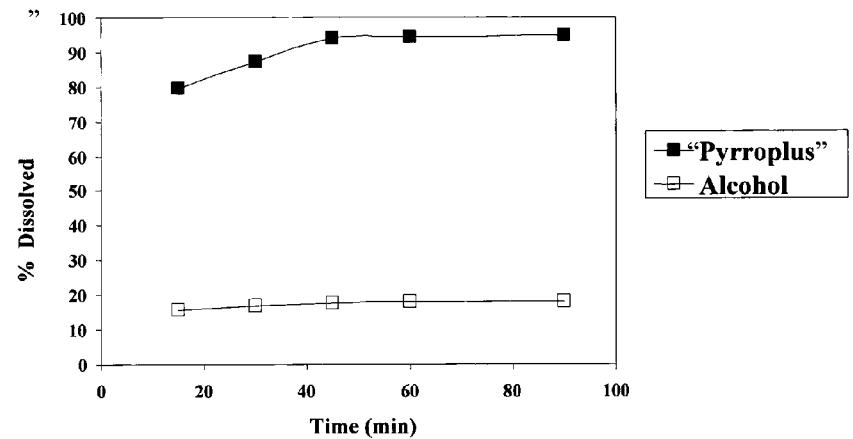
FIG. 1: Comparative dissolution profiles of the pharmaceutical composition prepared by "Pyrroplus Manufacturing Process" and the pharmaceutical formulation using ethanol as solubilizing agent.

A major object of the present invention is to apply a novel method for the preparation of improved pharmaceutical compositions comprising poorly water soluble active ingredients.

We present as a feature of the invention a pharmaceutical composition for oral administration comprising a poorly water-soluble active ingredient adducted to a dissolution enhancing agent, that is a pharmaceutical excipient bearing a cyclic amide moiety, preferably a 2-pyrrolidone-functional excipient and more preferably 2-pyrrolidone, N-methyl-2-pyrrolidone and polyvinyl pyrrolidone, in order to afford improved water solubility.

For the purposes of the present invention, a pharmaceutical composition comprising a poorly water soluble active ingredient is considered to be improved if said composition achieves increased solubility of said active ingredient, thereby generating the possibility of greater bioavailability.

For the purposes of the present invention, a pharmaceutical composition comprising an active ingredient with poor dissolution is considered to be improved if said composition achieves increased dissolution of said active ingredient, thereby generating the possibility of greater bioavailability.

In accordance with the above objects, a new technological platform "Pyrroplus Manufacturing Process" for manufacturing pharmaceutical dosage forms comprising poorly water soluble active ingredients, or active ingredients that have poor dissolution, is provided which combines wet and dry granulation processes. Said method employs the use of 2-pyrrolidone-based excipients as a solubilizing agent in combination with silicon dioxide and enhances the solubility of the active pharmaceutical ingredients.

Another aspect of the present invention is to provide solid pharmaceutical formulations for oral administration which are simple to manufacture, cost effective, possess good pharmacotechnical properties and linearity.

The following examples present the implementation of "Pyrroplus" technique to a number of poorly water soluble active pharmaceutical ingredients showing a significant increase in their solubility. For all the compositions presented below, excipients were chosen carefully to give appropriate dissolution rate and stability of the finished dosage form. The chosen quantities of each excipient have been derived after a series of tests and are considered the most appropriate regarding the solubility and the formulation characteristics.

By the use of the term active ingredient we mean those active ingredients that are poorly water soluble. In addition, we mean those active ingredients that have poor dissolution properties. In addition we mean those active ingredients that have a carboxy group. Preferred active ingredients are Atorvastatin, Leflunomide, Raloxifene and Tadalafil.

By the use of the term "poorly water soluble" we mean active ingredients which have a solubility of less than or equal to 0.1 mg/ml in water as defined in the US or European Pharmacopoeia. Among poorly water soluble active ingredients for use in the invention are active ingredients of the Biopharmaceutical Classification System (BSC guidance for industry of the U.S. Food and Drug Administration), class II active ingredients, characterized by low solubility and high permeability, and class IV active ingredients, characterized by low solubility and low permeability.

For a particular active ingredient its dissolution speed may depend on its crystallinity, or lack thereof, in case of amorphous solids, or other physical factors unconnected with its absolute solubility in a particular media. Amorphous forms generally have a higher dissolution speed than crystalline forms of the same active ingredient because the solvent can easily penetrate and dissolve more amount of amorphous form. The mechanism of action of "Pyrroplus" consists in the transformation of the active ingredients from crystalline to amorphous state. Thus, the invention can improve dissolution speed of active ingredients, especially of those that are crystalline.

Specific amounts of the cyclic amide moiety containing excipient and silicon dioxide were tested in order to determine the desirable amounts that enhance dissolution rate of poorly water soluble active ingredients. The composition of the present invention comprises at least 1%, at least 5%, at least 10%, at least 15% by weight, and at least 30%, 25% or 20% by weight of cyclic amide moiety containing excipient. The composition of the present invention comprises at least 1%, at least 5% and at least 10% and less than 20% and 15% by weight of silicon dioxide.

Moreover, the pharmaceutical composition of the present invention may also contain one or more additional formulation excipients. Those excipients that are required to be desired to be intimately mixed with the active ingredient, such as inside a granule, are called "internal phase excipients" and may be selected from one or more of the following; binders, disintegrants, diluents and glidants.

Binders are selected from the group consisting of Kollidon VA 64, carbomer, ethyl cellulose, gelatin, liquid glucose, guar gum, hydroxyethyl cellulose, methylcellulose and polydextrose. Most preferably, the composition comprises 1% to 15% by weight of a binder, preferably the binder is Kollidon VA 64.

Disintegrants are selected from the group consisting of crospovidone, carbon dioxide, carboxymethylcellulose calcium, carboxymethylcellulose sodium, croscarmelose sodium and guar gum. Most preferably, the composition comprises 1% to 15% by weight of a disintegrant, such as crospovidone, and additionally 1% to 5% by weight of a second disintegrant, preferably croscarmellose.

Diluents are selected from the group consisting of microcrystalline cellulose, dextrates, dextrose, fructose, mannitol, sorbitol, lactose, sucrose, xylitol, maltose and dicalcium phosphate anhydrous. Most preferably, the composition comprises 5% to 25% by weight of a diluent, preferably microcrystalline cellulose, or 1% to 20% by weight of a diluent, preferably lactose, or 1% to 15% by weight of a diluent, preferably dicalcium phosphate anhydrous, or a mixture of one or more.

Glidants are selected from the group consisting of colloidal silicon dioxide, calcium silicate and starch. Most preferably, the composition comprises 10% to 35% by weight of a glidant, preferably starch.

The excipients that are desired not to be intimately mixed with the active ingredient are the "external phase excipients" and sit in the composition but outside the internal phase, which may be a granule, and may be for example selected from one of more of the following; fillers, disintegrants and/or lubricants.

Disintegrants are selected from the group consisting of crospovidone, carbon dioxide, carboxymethylcellulose calcium, carboxymethylcellulose sodium, croscarmelose sodium, guar gum. Most preferably, the composition comprises 1% to 5% by weight of croscarmellose in the external phase.

Lubricants are selected from the group consisting of talc, magnesium stearate, calcium stearate, glyceryl behenate, hydrogenated castor oil, stearic acid, sodium lauryl sulfate. Most preferably, the composition comprises 0, 5% to 5% by weight of magnesium stearate.

EXAMPLES

Example 1

Tablet Comprising 20 Mg of Tadalafil (Composition 1)

Tablets comprising Tadalafil were prepared by "Pyrroplus Manufacturing Process". The composition of the tablets is illustrated in Table 1:

TABLE 1

Composition 1 produced by "Pyrroplus Manufacturing Process"

| Ingredients | mg per tablet | % content |
|---|---|---|
| Internal phase | | |
| Tadalafil | 20 | 3.0 |
| Pyrrolidone | 120 | 18.0 |
| Kollidon VA 64 | 40 | 6.0 |
| Crospovidone | 40 | 6.0 |
| Microcrystalline cellulose | 100 | 15.0 |
| Lactose monohydrate | 52 | 7.7 |
| Starch | 160 | 24.0 |
| Dicalcium phosphate anhydrous | 40 | 6.0 |
| Silicon dioxide | 60 | 9.0 |
| Croscarmellose | 15 | 2.2 |
| External phase | | |
| Croscarmellose | 15 | 2.2 |
| Mg-Stearate | 6 | 0.9 |
| Total | 668 | 100 |

The manufacturing process, as followed for preparing the Composition 1 consists of the following steps:

Dissolving Tadalafil in 2-pyrrolidone by stirring.

Mixing the obtained solution with the blend of silicon dioxide and the rest of internal phase excipients: Kollidon VA64, crospovidone, microcrystalline cellulose, lactose monohydrate, starch, dicalcium phosphate anhydrous, croscarmellose.

Wet granulation of the obtained mixture with the adequate quantity of ethanol.

Drying the wetted mass at 40° C.

Passing the dry granule through a sieve to achieve the desired granule size.

Mixing the dry granule with croscarmelose and magnesium stearate

Compressing the bulk into tablets of 668 mg average weight, in a tableting machine with oblong punches of 16 mm length an 8 mm width.

The bulk has good properties (tap, density, flow) and the tablets are characterized by excellent pharmacotechnical properties, such as homogeneity, compressibility, high hardness, low friability and quick disintegration time.

Pyrroplus Manufacturing Process" as described above, overcomes several problems associated with the low solubility of Tadalafil. More specifically, when Tadalafil is dissolved in 2-pyrrolidone its solubility increases and reaches high values. Conversely, using ethanol as solvent requires either increased amount of solvent or small quantity of Tadalafil, which both incommode the preparation of a pharmaceutical composition.

Table 2 illustrates the comparative solubility studies of the formulation of the present invention and a formulation produced by replacing 2-pyrrolidone with equal quantity of ethanol:

TABLE 2

Comparative dissolution profiles of Composition 1 and the pharmaceutical formulation prepared using ethanol as solubilizing agent

| Time (min) | % Dissolved using pyrrolidone | % Dissolved using ethanol |
|---|---|---|
| 15 | 79.35 | 15.53 |
| 30 | 86.96 | 16.92 |
| 45 | 94.05 | 17.63 |
| 60 | 94.90 | 18.09 |
| 90 | 94.43 | 18.25 |

The results indicate that "Pyrroplus" significantly increases the dissolution rate of Tadalafil (FIG. 1). More than 90% is released within 90 min using 2-pyrrolidone along with silicon dioxide while less than 20% is released when ethanol is used.

An important object of the present invention is to provide an immediate release composition that has an improved dissolution profile. The dissolution profile given from the dissolution test of the tablets in aqueous dissolution medium pH 4.5, 50 rpm is presented below.

TABLE 3

Dissolution results of Composition 1 in aqueous buffer at 50 rpm and at pH 4.5

| Time (min) | % Dissolved |
|---|---|
| 15 | 65.97 |
| 30 | 83.47 |
| 45 | 90.00 |

TABLE 3-continued

Dissolution results of Composition 1 in
aqueous buffer at 50 rpm and at pH 4.5

| Time (min) | % Dissolved |
|---|---|
| 60 | 91.90 |
| 90 | 92.65 |

According to the dissolution results, Composition 1 prepared by "Pyrroplus Manufacturing Process" exhibits a significant immediate release character as 80% of Tadalafil is dissolved within less than 30 min and about 90% within 45 min.

Furthermore, the effect of silicon dioxide in the dissolution rate and the granulation process was studied extensively. In particular, a certain formulation was prepared by excluding silicon dioxide. Summarizing the results it was shown that the solubility of Tadalafil reduced by 40% within 90 minutes. In addition, the texture of the formulation produced without using silicon dioxide was oily.

Figure 2:
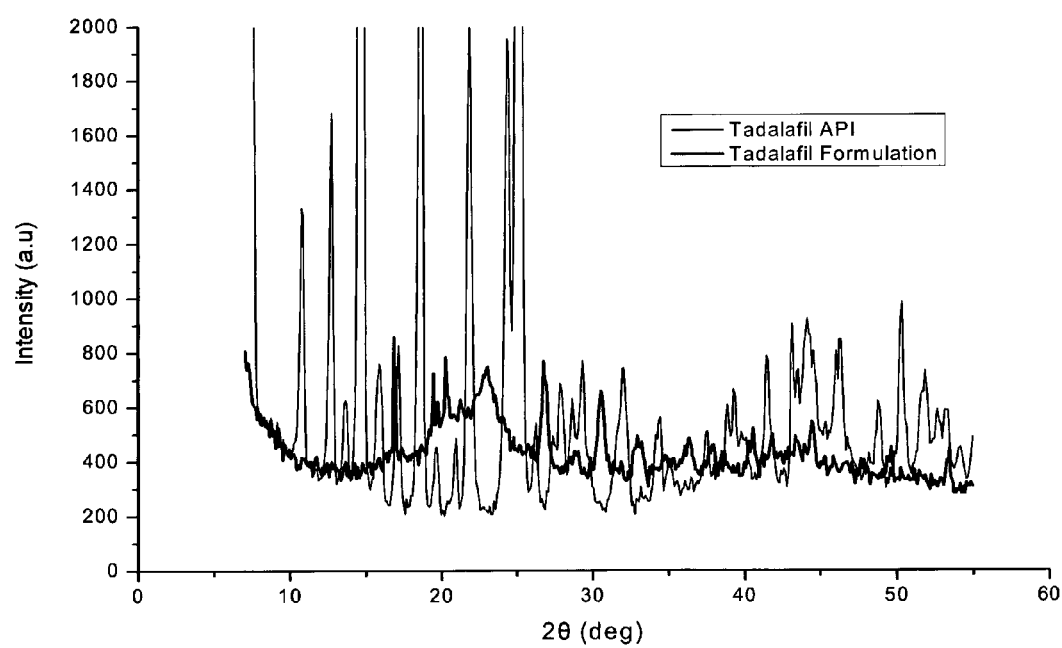
FIG. 2: Comparative XRD of pure Tadalafil and Tadalafil in the pharmaceutical composition produced by "Pyrroplus Manufacturing Process".
Figure 3:
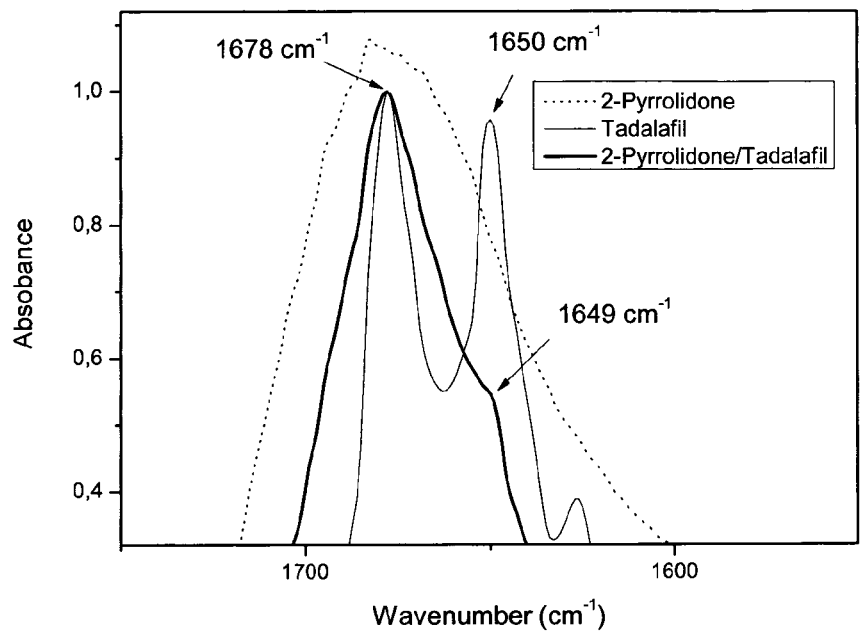
FIG. 3: Comparative FTIR of Tadalafil prior to and after dissolving in 2-pyrrolidone.

The mechanism of "Pyrroplus Manufacturing Process" has not yet been completely recognized. Based on the results of the solubility, and the XRD studies, the possible mechanism of action is a transformation of the active ingredient from crystalline to amorphous state (FIG. 2). In addition, FTIR studies confirm the interaction between the API and 2-pyrrolidone as it can also be seen from FIG. 3. The pure active ingredient absorbs at 1678 and 1650 cm$^{-1}$. The absorption at 1678 remains stable after the addition of 2-pyrrolidone whereas the second absorption almost disappears and only a small shoulder at 1649 cm$^{-1}$ can be detected in that area. This proves that one of the two carbonyl groups of the active ingredient interacts with the cyclic amide moiety of the excipient. Said interaction possibly occurs during the solvent evaporation and due to hydrogen bond interactions between active ingredient and cyclic amide moiety of the excipient. Since the active ingredient is in the amorphous state, it can form hydrogen bonds with the rest of the excipients of the mixture. These bonds maintain the active ingredient at an amorphous form, preventing it from recrystallizing. It is also worth mentioning that the large surface area of silicon dioxide, resulting in a large area of contact between the excipient and the active ingredient, supports the active ingredient to remain at its amorphous state which in general has a higher dissolution rate than the crystalline form.

The effect of the cyclic amide moiety containing excipient on the dissolution rate and in consequence on the bioavailability of the active ingredient can be attributed to several reasons. Firstly, its strongly hydrophilic character improves water penetration of the active ingredient. In addition, the absence of crystals (amorphous dispersion) requires lower level of energy for dissolution than the crystalline as all amorphous ingredients exhibit enhanced release. Moreover, hydrogen bonds and the molecular adduction of the active ingredient to cyclic amide moiety containing excipient leads to partial miscibility improving the hydrophilic characteristics of the active ingredient via interactions within the cyclic amide moiety containing excipient.

As shown above, silicon dioxide also performs an important additional role in the dissolution enhancement of the active ingredient. Its small particle size and large specific surface results in a large area of contact with the active ingredient aiding it to remain in its amorphous state. When incorporated in a pharmaceutical composition, a fine dispersion of amorphous particles of the active ingredient is being formed on its surface, resulting in a one-phase system. Said one-phase system improves the solubility of the active ingredient. It also has desirable flow characteristics that improve the flow properties of the dry powders.

Amorphous active ingredients should be cautiously formulated because they have a tendency to recrystallize, resulting in bioavailability that is not reproducible or decreases significantly after certain dosage periods due to degradation products. There is no such concern in the present formulation. The stability of the system is due to the formation of heteromolecular hydrogen bonds, which keep the molecules of the active ingredient ingredients frozen in the polymer matrix decreasing their mobility.

Therefore, in addition we present as a feature of the invention the use of a cyclic amide moiety containing excipient to stabilise an active ingredient in the amorphous state within a pharmaceutical composition.

Therefore, the cyclic amide moiety containing excipient and silicon dioxide have an important function in present formulation and contribute to an improved solid pharmaceutical dosage form produced by "Pyrroplus Manufacturing Process".

All the formulations presented below were also prepared following "Pyrroplus Manufacturing Process" as described in Example 1.

Example 2

Tablet Comprising 20 mg of Leflunomide (Composition 2)

TABLE 4

Composition 2 produced by "Pyrroplus Manufacturing Process"

| Ingredients | mg per tablet | % content |
|---|---|---|
| Internal phase | | |
| Leflunomide | 20 | 3.0 |
| Pyrrolidone | 120 | 18.0 |
| Kollidon VA 64 | 40 | 6.0 |
| Crospovidone | 40 | 6.0 |
| Microcrystalline cellulose | 100 | 15.0 |
| Lactose monohydrate | 52 | 7.7 |
| Starch | 160 | 24.0 |
| Dicalcium phosphate anhydrous | 40 | 6.0 |
| Silicon dioxide | 60 | 9.0 |
| Croscarmellose | 15 | 2.2 |
| External phase | | |
| Croscarmellose | 15 | 2.2 |
| Mg-Stearate | 6 | 0.9 |
| Total | 668 | 100 |

Figure 4:
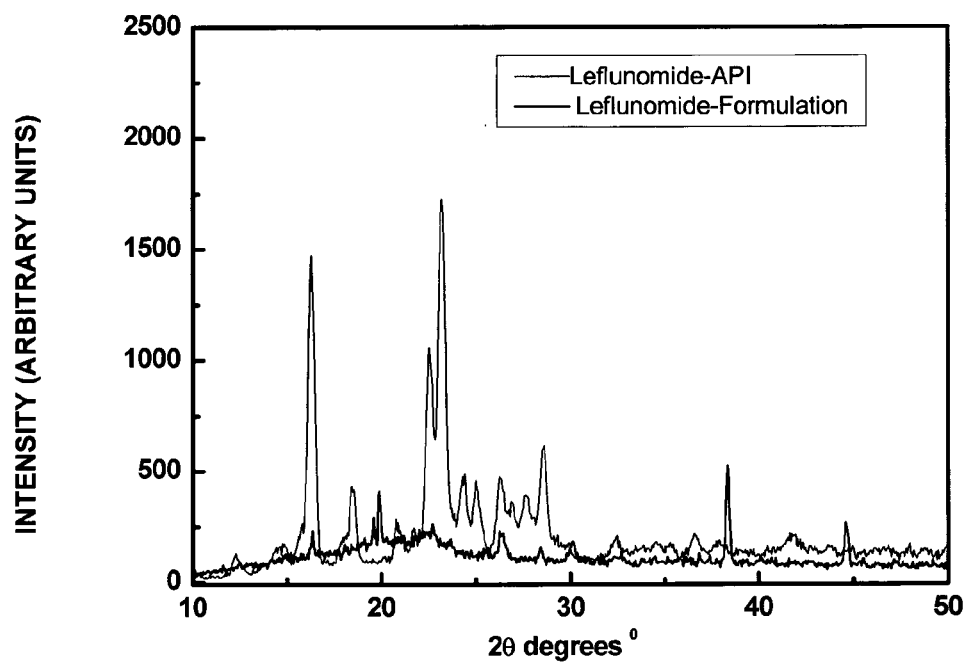
FIG. 4: Comparative XRD of pure Leflunomide and Leflunomide in the pharmaceutical composition produced by "Pyrroplus Manufacturing Process".

Comparative XRD of pure Leflunomide and Leflunomide in a pharmaceutical composition produced by "Pyrroplus Manufacturing Process" is shown in FIG. 4. The dissolution profile of the tablet above is illustrated in Table 5.

TABLE 5

Dissolution results of Composition 2 in aqueous buffer
at 50 rpm and at pH 1.2

| Time (min) | % Dissolved |
|---|---|
| 15 | 82.84 |
| 30 | 86.76 |
| 45 | 90.40 |

TABLE 5-continued

Dissolution results of Composition 2 in aqueous buffer at 50 rpm and at pH 1.2

| Time (min) | % Dissolved |
|---|---|
| 60 | 90.47 |
| 90 | 90.07 |

Example 3

Tablet Comprising 20 mg Raloxifene (Composition 3)

TABLE 6

Composition 3 produced by "Pyrroplus Manufacturing Process"

| Ingredients | mg per tablet | % content |
|---|---|---|
| Internal phase | | |
| Raloxifene | 20 | 3.0 |
| Pyrrolidone | 120 | 18.0 |
| Kollidon VA 64 | 40 | 6.0 |
| Crospovidone | 40 | 6.0 |
| Microcystalline cellulose | 100 | 15.0 |
| Lactose monohydrate | 52 | 7.7 |
| Starch | 160 | 24.0 |
| Dicalcium phosphate anhydrous | 40 | 6.0 |
| Silicon dioxide | 60 | 9.0 |
| Crosscarmellose | 15 | 2.2 |
| External phase | | |
| Crosscarmellose | 15 | 2.2 |
| Mg-Stearate | 6 | 0.9 |
| Total | 668 | 100 |

Figure 5:
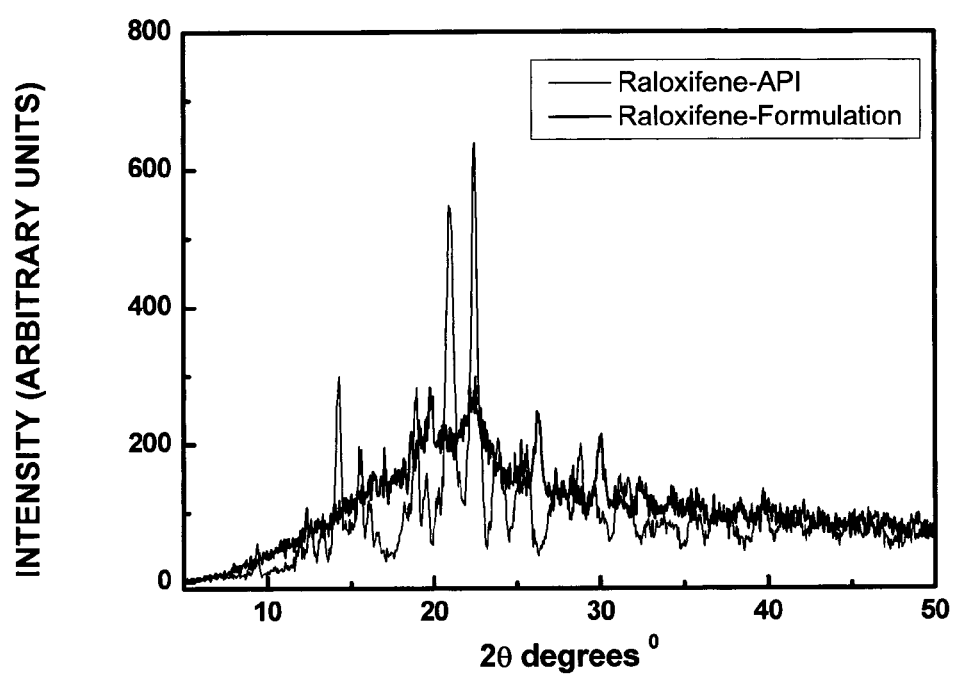
FIG. 5: Comparative XRD of pure Raloxifene and Raloxifene in the pharmaceutical composition produced by "Pyrroplus Manufacturing Process".

Comparative XRD of pure Raloxifene and Raloxifene in a pharmaceutical composition produced by "Pyrroplus Manufacturing Process" is shown in FIG. 5. The dissolution profile of the tablet above is illustrated in Table 7.

TABLE 7

Dissolution results of Composition 3 in aqueous buffer at 50 rpm and at pH 1.2

| Time (min) | % Dissolved |
|---|---|
| 15 | 60.00 |
| 30 | 65.14 |
| 45 | 68.68 |
| 60 | 69.72 |
| 90 | 69.71 |

Example 4

Tablet Comprising 20 mg Atorvastatin (Composition 4)

TABLE 8

Composition 4 produced by "Pyrroplus Manufacturing Process"

| Ingredients | mg per tablet | % content |
|---|---|---|
| Internal phase | | |
| Atorvastatin | 20 | 3.0 |
| Pyrrolidone | 120 | 18.0 |
| Kollidon VA 64 | 40 | 6.0 |
| Crospovidone | 40 | 6.0 |
| Microcrystalline cellulose | 100 | 15.0 |
| Lactose monohydrate | 52 | 7.7 |
| Starch | 160 | 24.0 |
| Dicalcium phosphate anhydrous | 40 | 6.0 |
| Silicon dioxide | 60 | 9.0 |
| Croscarmellose | 15 | 2.2 |
| External phase | | |
| Crosscarmellose | 15 | 2.2 |
| Mg-Stearate | 6 | 0.9 |
| Total | 668 | 100 |

The dissolution profile of the tablets above is illustrated in Table 9.

TABLE 9

Dissolution profile of Composition 4 in aqueous buffer at 50 rpm and at pH 1.2

| Time (min) | % Dissolved |
|---|---|
| 15 | 41.92 |
| 30 | 52.40 |
| 45 | 57.03 |
| 60 | 58.37 |
| 90 | 58.00 |

From the above dissolution results it is obvious that the release rate of the active ingredients is significantly high, facilitating the manufacturing procedure and generating the provisions of enhanced bioavailability.

The optimization of the dissolution profile and the enhanced bioavailability of the active ingredients achieved by said method offers the opportunity to use it widely in pharmaceutical production and overcomes the problems caused by the solubility deficiencies of many active ingredients.

While the present invention has been described with respect to the particular embodiments, it will be apparent to those skilled in the art that various changes and modifications may be made in the invention without departing from the spirit and scope thereof, as defined in the appended claims.

The invention claimed is:

1. A pharmaceutical composition for oral administration comprising a poorly water soluble active ingredient, wherein the poorly water soluble active ingredient has a solubility of less than or equal to 0.1 mg/mL in water, and from about 15% to about 25% by weight of 2-pyrrolidone and from about 5% to about 15% by weight of silicon dioxide.

2. The pharmaceutical composition according to claim 1, wherein the poorly water soluble active ingredient is a class II active ingredient or class IV active ingredient according to the Biopharmaceutical Classification System.

3. The pharmaceutical composition according to claim 1, wherein the poorly water soluble active ingredient is selected from Atorvastatin, Leflunomide, Raloxifene and Tadalafil.

4. The pharmaceutical composition according to claim 1, wherein it further comprises at least one pharmaceutically acceptable excipient selected from binders, disintegrants, diluents, glidants and lubricants.

5. A process for the preparation of solid dosage forms for oral administration comprising a poorly water soluble active ingredient, wherein the poorly water soluble active ingredient has a solubility of less than or equal to 0.1 mg/mL in water, and from about 15% to about 25% by weight of 2-pyrrolidone and from about 5% to about 15% by weight of silicon dioxide, which comprises:
   i) dissolving and/or mixing the active ingredient with t 2-pyrrolidone, optionally by stirring;
   ii) mixing the obtained solution/mixture with silicon dioxide, and optionally adding other internal phase excipients;
   iii) wet or dry granulation of the obtained mixture, optionally with ethanol; and, optionally, drying the wetted mass, if required.

6. The process according to claim 5, wherein the poorly water soluble active ingredient is a class II active ingredient or class IV active ingredient according to the Biopharmaceutical Classification System.

7. The process according to claim 5, wherein the poorly water soluble active ingredient is selected from Atorvastatin, Leflunomide, Raloxifene and Tadalafil.

* * * * *